(12) United States Patent
Zuber

(10) Patent No.: US 11,273,268 B2
(45) Date of Patent: Mar. 15, 2022

(54) NICOTINE INHALER SYSTEM

(71) Applicant: PHILIP MORRIS PRODUCTS S.A., Neuchatel (CH)

(72) Inventor: Gerard Zuber, Boulens (CH)

(73) Assignee: Philip Morris Products S.A., Neuchâtel (CH)

( * ) Notice: Subject to any disclaimer, the term of this patent is extended or adjusted under 35 U.S.C. 154(b) by 317 days.

(21) Appl. No.: 16/309,739

(22) PCT Filed: Jun. 14, 2017

(86) PCT No.: PCT/IB2017/053545
§ 371 (c)(1),
(2) Date: Dec. 13, 2018

(87) PCT Pub. No.: WO2018/007886
PCT Pub. Date: Jan. 11, 2018

(65) Prior Publication Data
US 2019/0116879 A1    Apr. 25, 2019

(30) Foreign Application Priority Data
Jul. 7, 2016    (EP) ..................... 16178327

(51) Int. Cl.
*A61M 11/02*    (2006.01)
*A61M 15/00*    (2006.01)
(Continued)

(52) U.S. Cl.
CPC ............. *A61M 11/02* (2013.01); *A24B 15/16* (2013.01); *A24B 15/167* (2016.11); *A24F 7/02* (2013.01);
(Continued)

(58) Field of Classification Search
CPC ............ A61M 15/0035; A61M 15/003; A61M 15/0008; A61M 15/06; A61M 15/0063;
(Continued)

(56) References Cited

U.S. PATENT DOCUMENTS 1,687,323 A * 10/1928 Cook ...................... A61M 5/24
604/201
1,789,921 A * 1/1931 Adam ................... A61M 15/00
128/203.23
(Continued)

FOREIGN PATENT DOCUMENTS

CN    101754780 A    6/2010
CN    103501847 A    1/2014
(Continued)

OTHER PUBLICATIONS

Extended European Search Report for EP 16178327.9, issued by the European Patent Office; 8 pgs.
(Continued)

*Primary Examiner* — Victoria Murphy
(74) *Attorney, Agent, or Firm* — Mueting Raasch Group

(57) ABSTRACT

An inhaler system suitable for providing nicotine particles includes a mouthpiece portion removably coupled to a distal end portion. The mouthpiece portion includes a capsule cavity and a mouthpiece air channel extending from the mouthpiece end to the capsule cavity. The distal end portion includes a piercing element coupled to the distal end portion and a resealable membrane configured to seal the capsule cavity when the mouthpiece portion is coupled to the distal end portion. The resealable membrane is configured to reseal when the piercing element moves out of the resealable membrane.

12 Claims, 2 Drawing Sheets

Figure 1:
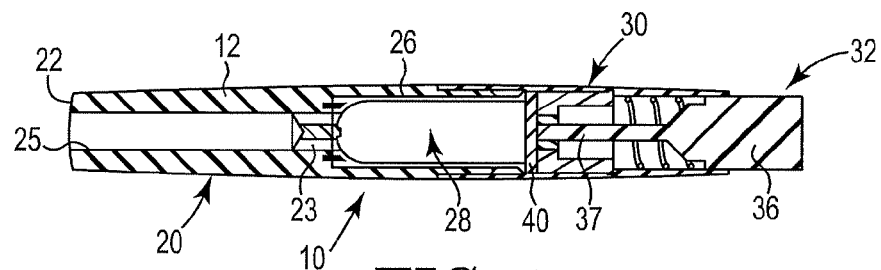

(51) Int. Cl.
*A61M 15/06* (2006.01)
*A24B 15/16* (2020.01)
*A24F 42/20* (2020.01)
*A24F 42/60* (2020.01)
*A24B 15/167* (2020.01)
*A24F 7/02* (2006.01)

(52) U.S. Cl.
CPC .............. *A24F 42/20* (2020.01); *A24F 42/60* (2020.01); *A61M 15/00* (2013.01); *A61M 15/003* (2014.02); *A61M 15/0028* (2013.01); *A61M 15/06* (2013.01); *A61M 2202/064* (2013.01)

(58) Field of Classification Search
CPC ........ A61M 2202/064; A61M 2206/16; A61M 11/02; A61M 15/00; A61M 15/0028; A61M 15/0043; A61M 15/0045; A61M 31/00; A24F 47/002; A24F 7/02; A24F 42/20; A24F 42/60; A24F 47/00; A24B 15/16; A24B 15/167; A24B 15/186; A24B 15/243
See application file for complete search history.

(56) References Cited

U.S. PATENT DOCUMENTS

| | | | | | |
|---|---|---|---|---|---|
| 2,503,732 | A | * | 4/1950 | Heisterkamp | A61M 15/0015 128/203.15 |
| 2,830,597 | A | * | 4/1958 | Kummli | A24F 42/60 131/273 |
| 2,860,638 | A | * | 11/1958 | Bartolomeo | A24F 42/20 128/202.21 |
| 2,911,123 | A | * | 11/1959 | Saccomanno | A61M 5/162 215/247 |
| 3,012,694 | A | * | 12/1961 | Johnston | A61M 15/00 222/5 |
| 3,030,955 | A | * | 4/1962 | Gossett | A61M 39/04 604/404 |
| 3,365,102 | A | * | 1/1968 | Castleberry | A24F 42/20 222/83.5 |
| 3,906,950 | A | * | 9/1975 | Cocozza | A61M 15/0028 128/203.15 |
| 4,069,819 | A | * | 1/1978 | Valentini | A61M 15/0028 128/203.15 |
| 4,111,326 | A | * | 9/1978 | Percarpio | A61B 5/15003 215/247 |
| 4,338,931 | A | | 7/1982 | Cavazza | |
| 4,511,353 | A | * | 4/1985 | Theeuwes | A61M 5/1407 604/251 |
| 4,695,274 | A | * | 9/1987 | Fox | A61M 5/3271 604/198 |
| 4,735,217 | A | | 4/1988 | Gerth et al. | |
| 4,790,305 | A | * | 12/1988 | Zoltan | A61M 15/0086 128/200.23 |
| 5,122,123 | A | * | 6/1992 | Vaillancourt | A61M 39/14 604/192 |
| 5,135,753 | A | * | 8/1992 | Baker | A61K 9/0056 424/434 |
| 5,279,607 | A | * | 1/1994 | Schentag | A61B 5/0031 604/114 |
| 5,362,496 | A | * | 11/1994 | Baker | A61K 9/0043 424/434 |
| 5,366,122 | A | * | 11/1994 | Guentert | A61M 13/00 128/200.22 |
| 5,441,060 | A | * | 8/1995 | Rose | A24F 42/60 131/271 |
| 5,746,227 | A | | 5/1998 | Rose et al. | |
| 5,989,217 | A | | 11/1999 | Ohki et al. | |
| 6,102,036 | A | * | 8/2000 | Slutsky | A61M 15/0045 128/202.21 |
| 6,550,477 | B1 | | 4/2003 | Casper et al. | |
| 8,360,057 | B2 | * | 1/2013 | Ganem | A61M 15/0063 128/203.21 |
| 9,428,314 | B2 | * | 8/2016 | Luciano, Jr. | B65D 75/527 |
| 2002/0134373 | A1 | * | 9/2002 | Gonda | A61M 15/0028 128/203.15 |
| 2003/0075172 | A1 | * | 4/2003 | Johnson | A61P 9/12 128/200.24 |
| 2003/0140923 | A1 | * | 7/2003 | Taylor | A61M 15/0043 128/203.12 |
| 2003/0150453 | A1 | * | 8/2003 | Edwards | A61M 15/0028 128/203.21 |
| 2004/0055613 | A1 | * | 3/2004 | Horian | A61M 15/06 131/194 |
| 2005/0022813 | A1 | * | 2/2005 | Alston | A61M 15/0028 128/203.21 |
| 2005/0056280 | A1 | * | 3/2005 | Alston | A61M 15/0031 128/203.21 |
| 2005/0238708 | A1 | * | 10/2005 | Jones | A61M 15/0028 424/451 |
| 2006/0147389 | A1 | * | 7/2006 | Staniforth | A61M 11/001 424/46 |
| 2007/0131576 | A1 | * | 6/2007 | Ehling | B65D 75/527 206/528 |
| 2007/0221216 | A1 | * | 9/2007 | Ganem | A61M 15/0028 128/203.12 |
| 2008/0241255 | A1 | | 10/2008 | Rose et al. | |
| 2008/0286341 | A1 | * | 11/2008 | Andersson | A61K 9/2873 424/440 |
| 2009/0025721 | A1 | * | 1/2009 | Ellwanger | A61M 15/0025 128/203.15 |
| 2009/0032427 | A1 | * | 2/2009 | Cheu | A61M 15/0033 206/438 |
| 2009/0277446 | A1 | * | 11/2009 | Walz | A61M 15/0028 128/203.15 |
| 2009/0293873 | A1 | * | 12/2009 | Djupesland | A61M 15/0041 128/203.15 |
| 2010/0275917 | A1 | | 11/2010 | Kuhn et al. | |
| 2010/0300439 | A1 | * | 12/2010 | Djupesland | A61M 15/08 128/203.15 |
| 2011/0005523 | A1 | * | 1/2011 | Lalor | A61K 38/2026 128/203.15 |
| 2011/0220106 | A1 | * | 9/2011 | Ganem | A61M 15/0028 128/203.21 |
| 2011/0277752 | A1 | | 11/2011 | Cheu et al. | |
| 2012/0145150 | A1 | * | 6/2012 | Donovan | A61M 15/0021 128/203.15 |
| 2014/0088044 | A1 | | 3/2014 | Rigas et al. | |
| 2014/0182587 | A1 | | 7/2014 | Dunne et al. | |
| 2014/0190496 | A1 | | 7/2014 | Wensley et al. | |
| 2014/0251326 | A1 | | 9/2014 | Terry et al. | |
| 2014/0345634 | A1 | * | 11/2014 | Zuber | A24D 1/20 131/329 |
| 2017/0007766 | A1 | * | 1/2017 | Basile | A61M 5/5086 |
| 2017/0035108 | A1 | * | 2/2017 | Zinovik | A24F 42/20 |
| 2017/0135397 | A1 | * | 5/2017 | Buehler | A61M 15/06 |
| 2018/0007972 | A1 | * | 1/2018 | Thorens | A61M 15/003 |

FOREIGN PATENT DOCUMENTS

| | | | |
|---|---|---|---|
| CN | 104602552 A | 5/2015 | |
| CN | 204362977 U | 6/2015 | |
| CN | 105492056 A | 4/2016 | |
| EA | 200701646 A1 | 2/2008 | |
| EP | 2 186 537 A1 | 5/2010 | |
| EP | 2 399 637 A1 | 12/2011 | |
| EP | 2719415 A1 | 4/2014 | |
| GB | 1396258 A | 6/1975 | |
| GB | 2 461 008 A | 12/2009 | |
| JP | S49-130094 A | 12/1974 | |
| WO | WO 91/01656 A1 | 2/1991 | |
| WO | WO-9826828 A2 * | 6/1998 | ........ A61M 15/0008 |
| WO | WO-2004091707 A2 * | 10/2004 | ........ A61M 15/0033 |
| WO | WO 2006/062651 A1 | 6/2006 | |
| WO | WO 2010/052323 A2 | 5/2010 | |
| WO | WO 2012/120487 A2 | 9/2012 | |

(56) References Cited

FOREIGN PATENT DOCUMENTS

| WO | WO 2013/159245 A1 | 10/2013 |
| WO | WO 2014/150826 A1 | 9/2014 |
| WO | WO 2015/004227 A1 | 1/2015 |

OTHER PUBLICATIONS

International Search Report and Written Opinion for PCT/IB2017/053545; issued by the European Patent Office; 15 pgs.
International Preliminary Report on Patentability for PCT/IB2017/053545; issued by the European Patent Office; 6 pgs.
Hall, R.L. & Oser, B.L., "Recent Progress in the Consideration of Flavoring Ingredients under the Food Additive Amendments 3. Graf substances," *Food Technology*, Feb. 1965: p. 151-197.
Cohen et al., "GRAS flavoring substances 27," *Food Technology*, Aug. 2015: p. 40-59.
Russian Office Action and Search Report for RU 2018144596, issued by the Russian Patent Office dated Jul. 27, 2020; 5 pgs.
Chinese Office Action issued in CN 201780038637.1 by the China National Intellectual Property Administration dated Nov. 19, 2020; 6 pgs.
Japanese Office Action issued for JP 2018-563609 by the Japanese Patent Office dated Apr. 15, 2021, 13 pgs. including English Translation.

\* cited by examiner

NICOTINE INHALER SYSTEM

This application is the § 371 U.S. National Stage of International Application No. PCT/IB2017/053545, filed 14 Jun. 2017, which claims the benefit of European Application No. 16178327.9, filed 7 Jul. 2016, the disclosures of which are incorporated by reference herein in their entireties.

This disclosure relates to a nicotine inhaler system that provides multi-use delivery of nicotine particles.

Nicotine particle inhalers are not always suitable to provide nicotine particles to the lungs at inhalation or air flow rates that are within conventional smoking regime inhalation or air flow rates. Nicotine particle inhalers do not always include nicotine particle consumable which is easily replaceable once consumed.

It is desirable to provide a nicotine inhaler system that provides multi-use delivery of nicotine particles. It is desirable that the nicotine inhaler system may include a modular component capsule receptacle that may be easily replaceable once consumed. It is desirable that the article facilitates delivery of nicotine particles to the consumer at conventional smoking regime inhalation or air flow rates. The nicotine inhaler system may alleviate one or more of the above mentioned problems.

This disclosure is directed to an inhaler system suitable for providing nicotine particles that includes a mouthpiece portion removably coupled to a distal end portion. The mouthpiece portion includes a capsule cavity and a mouthpiece air channel extending from the mouthpiece end to the capsule cavity. The distal end portion includes a piercing element coupled to the distal end portion and a resealable membrane configured to seal the capsule cavity when the mouthpiece portion is coupled to the distal end portion. The resealable membrane is configured to reseal when the piercing element moves out of the resealable membrane.

The inhaler system suitable for providing nicotine particles may include an inhaler body extending from a mouthpiece end to a distal end and include a mouthpiece portion removably coupled to a distal end portion. The mouthpiece portion extends between the mouthpiece end and a first mating end. The distal end portion extends between a second mating end and the distal end. The mouthpiece portion includes a capsule cavity defined within the first mating end and a mouthpiece air channel extending from the mouthpiece end to the capsule cavity. The distal end portion includes a piercing element coupled to the distal end portion and a resealable membrane sealing the capsule cavity at the first mating end when the mouthpiece end is coupled to the distal end. The piercing element is configured to move between a relaxed position and a piercing position. The piercing element extends into the capsule cavity in the piercing position. The resealable membrane is configured to reseal when the piercing element moves from the piercing position to the relaxed position.

Preferably a receptacle may be disposed within the capsule cavity. The receptacle being a replaceable article of the inhaler. The receptacle contains a capsule that may contain particles that include nicotine. The receptacle may be sealed with a membrane at a receptacle first end and define an air outlet at an opposing receptacle second end. The receptacle may include an air inlet. Air flow management through the inhaler system may cause the capsule to rotate and release nicotine particles (once pierced) into the airflow.

Preferably the resealable membrane contacts the receptacle first end. The resealable membrane may contact the membrane at a receptacle first end when the mouthpiece portion is couple to the distal end portion. The resealable membrane may prevent air flow into the receptacle first end through the membrane at a receptacle first end.

The receptacle and capsule article may be a modular component of the multi-use nicotine inhaler system. The article may be easily replaceable within the multi-use inhaler. Once consumed, the article may be removed from the multi-use inhaler and discarded.

Advantageously, the inhaler system described herein provides a re-usable modular component approach when combined with a consumable receptacle containing a capsule. The resealable membrane ensures the air flow path though the inhaler system originates from the air inlets and exits thorough the mouthpiece air channel. This air flow management ensures that the capsule may rotate during inhalation and consumption. This rotation may suspend and aerosolize the nicotine particles in the inhalation air moving through the inhaler system. The nicotine particles may be delivered with the inhaler at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg 151-197, and in the GRAS flavoring substances 27 S. M. Cohen et al., Food Technology August 2015 pg. 40-59, and intervening GRAS Flavoring Substances publications 4 to 26. For the purpose of this disclosure, nicotine is not considered as a flavourant or flavour.

The size of a particle, stated herein, preferably refers to the aerodynamic diameter of the particle. The aerodynamic diameter of the particles is preferably measured with a cascade impactor.

The inhaler system described herein may be combined with one or more modular nicotine particle delivery consumables to deliver the nicotine particles to a consumer. A plurality of these modular nicotine particle delivery consumables (similar of different formulation or flavors) may be combined with an inhaler system to form a kit.

An inhaler system includes a mouthpiece portion removably coupled to a distal end portion. The mouthpiece portion includes a capsule cavity and a mouthpiece air channel extending from the mouthpiece end to the capsule cavity. The distal end portion includes a piercing element coupled to the distal end portion and a resealable membrane configured to seal the capsule cavity when the mouthpiece portion is coupled to the distal end portion. The resealable membrane is configured to reseal when the piercing element moves out of the resealable membrane.

The inhaler system includes an inhaler body extending between a mouthpiece portion and a distal end portion. An inhaler receptacle cavity or capsule cavity may be defined within the inhaler body between the mouthpiece portion and the distal end portion. A modular nicotine particle delivery consumable or receptacle article (receptacle containing a capsule containing particles including nicotine) may define an outer surface that mates with the inhaler receptacle cavity. A consumer may access the inhaler receptacle cavity to insert the modular receptacle article into the inhaler receptacle cavity or replace a depleted modular receptacle article with a full or un-used modular receptacle article into the inhaler receptacle cavity. An air inlet may extend through the inhaler body and into the inhaler receptacle cavity. A mouthpiece air channel is fluidly connected to the inhaler receptacle cavity and a proximal end of the mouthpiece. The inhaler body may resemble a smoking article or cigarette in size and shape.

In some embodiments, a capsule alone is inserted into the capsule cavity. A consumer may access the inhaler capsule cavity to insert the capsule consumable into the inhaler capsule cavity or replace a capsule consumable with a full or un-used capsule consumable into the inhaler capsule cavity.

The air inlet or air inlets that extend through the inhaler body may mate or align with the air inlet or air inlets that extend through the sidewall of the receptacle article placed into the inhaler receptacle cavity. The modular receptacle article air outlet extending thought the receptacle second end may mate or align with the mouthpiece air channel of the inhaler body. Once the modular receptacle article is placed into the inhaler receptacle cavity, air may flow through the modular receptacle article from the air inlet through the cavity and through the air outlet onto the mouthpiece air channel.

The resealable membrane may be fixed to the distal end and form a portion of the second mating end of the distal portion. The resealable membrane may separate the piercing element from the capsule cavity. The resealable membrane may contact the receptacle article when the mouthpiece portion is coupled to the distal portion. The resealable membrane may secure the receptacle article within the inhaler receptacle cavity. The resealable membrane may contact the membrane of the receptacle. The piercing element may pierce both the resealable membrane and the membrane of the receptacle when piercing the capsule contained within the receptacle article. When the piercing element moves back to its relaxed position and out of the resealable membrane, being spaced apart from the resealable membrane, the resealable membrane may reseal and prevent air from passing into the receptacle article through the void created in the membrane of the receptacle by the piercing element. Preferably the resealable membrane provides an air tight seal. The resealable membrane may provide an air tight seal after being pierced by the piercing element. The resealable membrane may provide an air tight seal while being pierced by the piercing element.

The distal portion is coupled to the piercing element. The distal portion may surround a portion of the piercing element. The piercing element may move along a longitudinal axis between a piercing (activated) position and a relaxed position. A biasing element may maintain the piercing element in the relaxed position. The biasing element may be a spring member. The biasing element may compress when the piercing element is pressed into the piercing position. Releasing the piercing element allows the biasing element to force the piercing element back to the relaxed position.

The piercing element may be a rigid element capable of piercing the resealable membrane and a capsule contained within the receptacle article or capsule cavity. The piercing element may be a metal element such as a needle.

The resealable membrane contacts the membrane of the receptacle and may effectively seal the void created in the membrane of the receptacle by the piercing element. Thus air flow through the inhaler system may not pass though the pierced membrane of the receptacle.

The resealable membrane is configured to close a void created in the resealable membrane created by a piercing element such as a needle. The resealable membrane may be pierced and seal or close the void a plurality of times, such as at least about 3 three times, or at least about 5 times, or at least about 10 times or at least about 20 times. The void is created through the thickness of the resealable membrane. The resealable membrane may have a thickness in a range from about 0.1 to about 5 millimeters, or from about 0.5 to about 2 millimeters. The resealable membrane may be formed of any resilient material. Resealable membranes may include a septum-like element. Resealable membranes may be formed of elastic material such as rubber, silicone, metal foil co-laminated with a polymer, or latex and the like.

The inhaler system includes a mouthpiece portion removably coupled to a distal end portion. The mouthpiece portion has a first mating end that fits or mates with a second mating end of the distal portion. The first mating end couples to the second mating end. The first mating portion may snap-fit to the second mating end. The first mating portion may screw onto or be in threaded engagement with the second mating end. The first mating portion may form an air tight fit or connection with the second mating end.

A modular receptacle article may be configured to be replaceably disposed within the inhaler receptacle cavity or capsule cavity defined in the first mating end of the mouthpiece portion. The modular receptacle article includes a receptacle defining a cavity. A capsule is disposed within the cavity. The receptacle is configured to contain the capsule within the cavity. The cavity may have a circular cross-section extending along at least a portion of the cavity length. The cavity may have a central axis or centroid longitudinal axis. Preferably the cavity has a shape similar to the shape of the capsule. The cavity may have a circular cross-sectional shape and a first diameter and the capsule may have a second diameter that is less than the first diameter. The second diameter may be in a range from about 80% to about 99% of the first diameter, or the second diameter may be in a range from about 90% to about 98% of the first diameter.

The receptacle includes a receptacle second end that is configured to contain the capsule and prevent the capsule from passing through the receptacle second end. The receptacle second end may be defined by a lateral wall integral with the body of the receptacle. The receptacle second end may be defined by an end cap that is fixed to the body of the receptacle. One or more air outlets may extend through the receptacle second end to allow air to flow from the article cavity to the exterior of the receptacle.

A membrane may seal the receptacle first end. The capsule may be placed into the cavity of the receptacle through an open first end and then the membrane may seal the open first end to retain the capsule within the cavity of the article. The membrane may form a hermetic or airtight seal or barrier.

The membrane may be formed of a pierce-able material. The inhaler system piercing element passes through the membrane and punctures the capsule within the receptacle. The membrane may re-seal once the piercing element is retracted from the membrane. Alternatively, the membrane may not re-seal once the piercing element is retracted from the membrane and be formed of resealable materials described herein. Membranes that may not re-seal include metal foil, for example.

An air inlet may extend through the receptacle body and into the cavity. Air inlets through the inhaler body may align with or be in air communication with the air inlets that extend through the receptacle body. Air inlets may be disposed on one or both of the inhaler body mouthpiece portion and distal portion. Preferably these air inlets are adjacent to or form part of the first or second mating ends.

Air inlets that are on both the inhaler body mouthpiece portion and distal portion may align when the mouthpiece portion is coupled to the distal portion.

The cavity may have a length in a range from about 15 mm to about 25 mm or from about 20 mm to about 24 mm. The cavity may have an inner diameter in a range from about 5 mm to about 10 mm or from about 6 mm to about 8 mm. The cavity may have a length of about 20 mm and an inner diameter of about 6.6 mm when containing a capsule size 3 flat. The cavity may have a length of about 24 mm and an inner diameter of about 7.7 mm when containing a capsule size 1 flat.

The air inlet may be closer to the receptacle first end than the receptacle second end. The air inlet may be located within about 5 mm or within about 4 mm or within about 3 mm or within about 2 mm of the receptacle first end. The air inlet may be located from about 1 mm to about 5 mm of the receptacle first end or from about 2 mm to about 4 mm of the receptacle first end.

The air inlet may be off-set from the centroid longitudinal (central) axis of the receptacle cavity or capsule contained within the cavity. The off-set air inlet induces the capsule to rotate or spin within the receptacle article during inhalation by the consumer. The air inlet may be off-set from the longitudinal (central) axis of the capsule or receptacle cavity by about 1 mm or about 2 mm or about 3 mm or about 4 mm where the cavity may have an inner diameter of about 5 mm to about 10 mm or from about 6 mm to about 8 mm. The one or more air inlets may have a diameter from about 0.5 to about 1.5 mm or about 0.7 mm to about 0.9 mm. Preferably, the air inlet directs air tangentially to the outer diameter of the capsule contained within the receptacle article.

The receptacle article receptacle preferably has a circular cross-sectional shape extending (a length distance) along its central axis and forming a cylindrical receptacle. Preferably the receptacle defines a right circular cylinder with a radius and having a length extending along a central axis. The air inlet may enter the receptacle tangentially to the cylindrical receptacle. Two or more air inlets enter the receptacle cavity tangentially to the cylindrical receptacle. Preferably these air inlets oppose each other and a first air inlet directs air tangentially to the cylindrical receptacle in a first direction and the second air inlet directs air tangentially to the cylindrical receptacle in a second direction that opposes or is in the opposite direction as the first direction. These opposing air inlets may direct inhalation air at opposing sides of the capsule contained within the receptacle promoting the rotation of the capsule contained within the receptacle.

The capsule may be sealed within the receptacle article prior to consumption or placement into the inhaler system. The receptacle article may be contained within a sealed or airtight container or bag. The receptacle article may include one or more peelable seal layers to cover the one or more air inlets or one or more air outlets on the receptacle article. An air outlet seal layer may be disposed on the air outlet. This seal layer may be configured to be punctured or be peelable to expose the air outlet. An air inlet seal layer may be disposed on the air inlet. This seal layer may be configured to be punctured or be peelable to expose the air inlet. The inhaler system may include air inlet piercing element or an air outlet piercing element that are configured to puncture one or both of these seal layers upon insertion of the receptacle article into the inhaler receptacle cavity or upon activation of the inhaler.

The capsule may be configured to rotate about its' longitudinal or central axis when air flows through the inhaler system (from the air inlet through the receptacle to the air outlet). The capsule may be formed of an airtight material that may be pierced or punctured by the piercing element of the inhaler system. The capsule may formed of a metallic or polymeric material that serves to keep contaminates out of the capsule but may be pierced or punctured by a piercing element prior to consumption of the nicotine particles within the capsule. Preferably, the capsule is formed of a polymer material. The polymer material may be hydroxypropylmethylcellulose (HPMC). Preferably, the capsule is a size 1 to size 4 or a size 3 capsule.

The capsule contains solid nicotine particles (also referred to as "nicotine powder" or "particles comprising nicotine") and optional flavour particles. The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". Preferably, the capsule may contain enough nicotine particles to provide from about 5 to 50 inhalations or "puffs", or from about 10 to 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 5% wt nicotine up to about 30% wt, or from about 5% wt to about 25% wt, or from about 5% wt to about 20% wt, or from about 5% wt to about 15% wt, or from about 7% wt to about 13% wt, nicotine. Preferably, about 50 to about 150 micrograms of nicotine is delivered to the lungs of the user with each "puff".

The capsule may hold or contain at least about 5 mg of nicotine particles or at least about 10 mg of nicotine particles. Preferably, the capsule holds or contains less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles are present in an amount that provides the desired flavour to each inhalation or "puff" delivered to the user.

The nicotine particles may have any useful size distribution for inhalation delivery preferentially into the lungs of a user. The capsule may include other particles than the nicotine particles. The nicotine particles and the other particles form a powder system.

The capsule may hold or contain at least about 5 mg of a powder system or at least about 10 mg of a powder system. Preferably, the capsule holds or contains less than about 900 mg of a powder system, or less than about 300 mg of a powder system, or less than 150 mg of a powder system. The capsule may hold or contain from about 5 mg to about 300 mg of a powder system or from about 10 mg to about 200 mg of a powder system.

The powder system may have at least about 40% or at least about 60%, or at least about 80%, by weight of the powder system comprised in nicotine particles having a particle size of about 10 micrometers or less, or 5 micrometers or less, or in a range from about 1 micrometer to about 3 micrometers.

Nicotine in the powder system or nicotine particles is preferably a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid is leucine such as, L-leucine. Providing an amino acid such as L-leucine with the particles comprising nicotine, may reduce adhesion forces of the particles comprising nicotine and may reduce attraction between nicotine particles and thus reduce agglomeration of nicotine particles.

Similarly, adhesion forces to particles comprising flavour is also reduced thus agglomeration of nicotine particles with flavour particles is also reduced. The powder system described herein thus may be a free flowing material and possess a stable relative particle size of each powder component even when the nicotine particles and the flavour particles are combined.

The powder system may include flavour particles. The flavour particles may have any useful size distribution for inhalation delivery selectively into the mouth or buccal cavity of a user.

The powder system may have at least about 40%, or at least about 60%, or at least about 80%, by weight of the flavour of the powder system comprised in particles having a particle size of about 20 micrometers or greater. The powder system may have at least about 40% or at least about 60%, or at least about 80%, by weight of the flavour of the powder system comprised in particles having a particle size of about 50 micrometers or greater. The powder system may have at least about 40% or at least about 60%, or at least about 80%, by weight of the flavour of the powder system comprised in particles having a particle size in a range from about 50 micrometer to about 150 micrometers.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. Preferably the flavour or flavourant has flavour properties that enhance the experience of the nicotine component during consumption. Preferably, the flavour is chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound is magnesium stearate. Providing an adhesion reducing compound such as magnesium stearate with the flavour particle, especially coating the flavour particle, reduces adhesion forces of the particles comprising flavour and may reduce attraction between flavour particles and thus reduce agglomeration of flavour particles. Thus agglomeration of flavour particles with nicotine particles is also reduced. The powder system described herein thus may possess a stable relative particle size of the particles comprising nicotine and the particles comprising flavour even when the nicotine particles and the flavour particles are combined. The powder system preferably is free flowing.

Conventional formulations for dry powder inhalation typically contain carrier particles that serve to increase the fluidization of the active particles since the active particles may be too small to be influenced by simple airflow though the inhaler. The powder system may comprise carrier particles. These carrier particles may be a saccharide such as lactose or mannitol that have a particle size greater than about 50 micrometers. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates. In addition, since the nicotine is carrier-free or substantially free of a saccharide such as lactose or mannitol, the airflow path of the inhaler may have simple geometry or a simple configuration.

The nicotine powder and a flavour may be combined in a single capsule. As described above, the nicotine powder and a flavour may each have reduced adhesion forces that result in a stable powder formulation where the particle size of each component does not substantially change when combined.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler systems described herein are less complex and have a simplified storage and airflow path as compared to conventional dry powder inhalers. Advantageously, rotation of the capsule within the inhaler system aerosolizes the nicotine particles or powder system and may assist in maintaining a free flowing powder. Thus, this inhaler system does not require the typical high inhalation rates of conventional inhalers to deliver the nicotine particles described above deep into the lungs.

The inhaler system may use a flow rate of less than about 5 L/min or less than about 3 L/min or less than about 2 L/min or about 1.6 L/min. Preferably, the flow rate is in a range from about 1 L/min to about 3 L/min or from about 1.5 L/min to about 2.5 L/min. Preferably, the inhalation rate or flow rate is similar to that of Health Canada smoking regime, that is, about 1.6 L/min.

The inhaler system may be used by a consumer like smoking a conventional cigarette or vaping an electronic cigarette. Such smoking or vaping is characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Referring to FIG. 1, an inhaler system 10 includes a mouthpiece portion 20 removably coupled to a distal end portion 30. The mouthpiece portion 20 includes a capsule cavity 26 and a mouthpiece air channel 25 extending from the mouthpiece end 22 to the capsule cavity 26. A capsule cavity outlet air channel 23 couples the mouthpiece air channel 25 to the capsule cavity 26. The capsule cavity 26 is defined by a cavity wall 26. The distal end portion 30 includes a piercing element 36 coupled to the distal end portion 30 and a resealable membrane 40 configured to seal the capsule cavity 26 when the mouthpiece portion 20 is coupled to the distal end portion 30. The resealable membrane 40 is configured to reseal when the piercing element 36 or needle 37 moves out of the resealable membrane 40. One or more air inlets 28 pass through the cavity wall 26.

Figure 2:
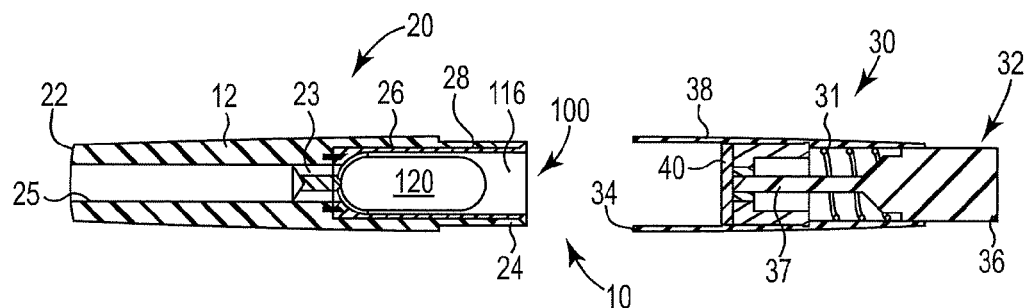
Figure 3:
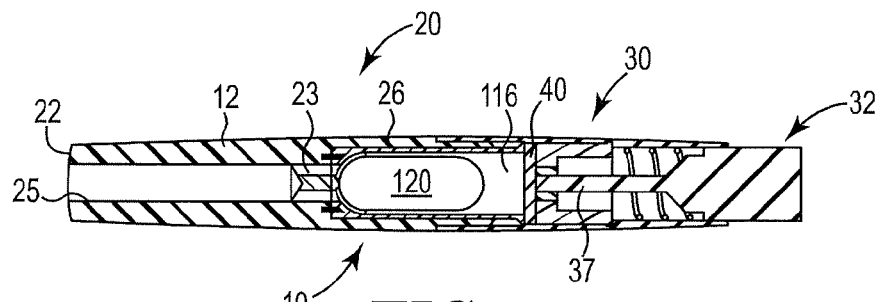
Figure 4:
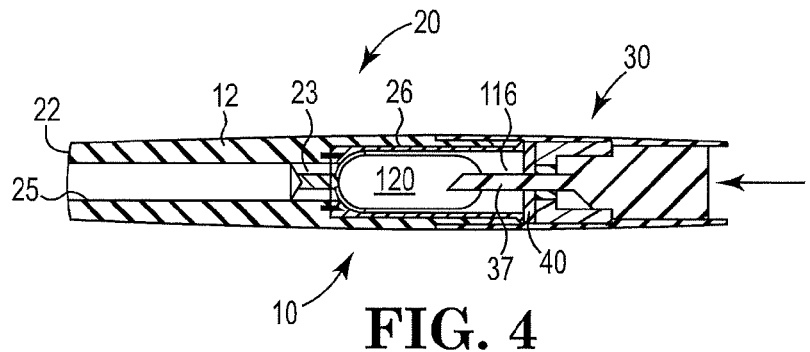

FIG. 2 is a schematic diagram of another illustrative inhaler system 10 with the distal end portion 30 un-coupled from the mouthpiece portion 20 and a nicotine powder delivery consumable 100 or receptacle article disposed within the capsule cavity 26. FIG. 3 is schematic diagram the illustrative inhaler system 10 with the distal end portion 30 coupled from the mouthpiece portion 20 and containing a capsule 120 within a receptacle article 100. FIG. 4 is schematic diagram the illustrative inhaler system 10 with the piercing element 36, 37 piercing the capsule 120 within a receptacle article 100 and piercing the resealable membrane 40.

The inhaler system 10 may include an inhaler body 12 extending from a mouthpiece end 22 to a distal end 32 and include a mouthpiece portion 20 removably coupled to a distal end portion 30. The mouthpiece portion 20 extends between the mouthpiece end 22 and a first mating end 24. The distal end portion 30 extends between a second mating end 34 and the distal end 32. The mouthpiece portion 20 includes a capsule cavity 26 defined within the first mating end 24 and a mouthpiece air channel 25 extending from the mouthpiece end 22 to the capsule cavity 26. A capsule cavity outlet air channel 23 couples the mouthpiece air channel 25 to the capsule cavity 26.

The distal end portion 30 includes a piercing element 36 coupled to the distal end portion 30 and a resealable membrane 40 sealing the capsule cavity 26 at the first mating end 24 when the mouthpiece end 20 is coupled to the distal end 30. The piercing element 36 is configured to move between a relaxed position (FIG. 3) and a piercing position (FIG. 4). The piercing element 37 extends into the capsule cavity 28 or 116 in the piercing position. The resealable membrane 40 is configured to reseal when the piercing element 37 moves from the piercing position to the relaxed position. A biasing element 31 or spring may provide the force to return the piercing element 36 to the relaxed position.

One or more air inlets 28, 38 on the inhaler body may align to provide inlet air to the capsule cavity 28. The one or more air inlets 28, 38 may extend through a side wall forming the capsule cavity 26. The air inlets 28, 38 may align with or be in air communication with the air inlets 117 of the receptacle article 100. The receptacle cavity 26 is configured to mate with the receptacle article 100. The detachable distal portion 30 may be removed from the mouthpiece portion 20 to expose the receptacle cavity 26 to replace the modular and used or depleted receptacle article 100 with an un-used or full receptacle article 100.

Figure 5:
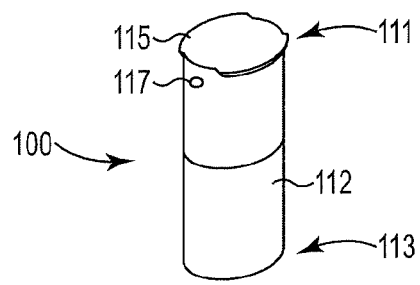
Figure 6:
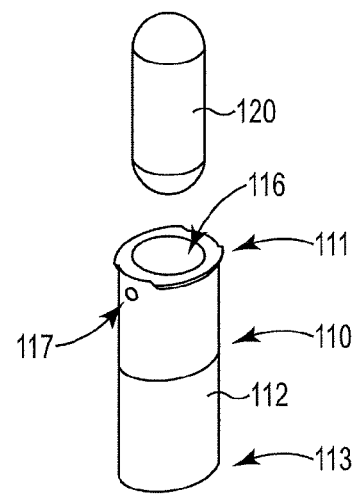

FIG. 5 and FIG. 6 illustrative a nicotine powder delivery consumable 100 or receptacle article. The nicotine powder delivery consumable or receptacle article 100 includes a receptacle 110 having a body or sidewall 112 extending from a receptacle first end 111 to an opposing receptacle second end 113 and defining a cavity 116. A capsule 120 is disposed within the cavity 116. The capsule 120 contains particles comprising nicotine. FIG. 6 illustrates the capsule 120 exploded away from the receptacle 110. The nicotine powder delivery consumable or receptacle article 100 may be formed by inserting the capsule 120 into the receptacle 110 and applying the membrane 115 on the receptacle first end 111 to seal the receptacle first end 111 and retain the capsule 120 within the receptacle 110.

The receptacle 110 includes a lateral wall fixed to or integral with the receptacle body or sidewall 112 and an air outlet extending through the lateral wall and into the cavity 116. A membrane 115 seals the receptacle first end 111. An air inlet 117 extends through the sidewall or body 112 and into the cavity 116. The air inlet 117 is proximate the receptacle first end 111 or closer to the receptacle first end 111 than the receptacle second end 113. The cavity 116 has a length value and a diameter value. The air inlet 117 is proximate the receptacle proximal end 111 a distance. The air inlet 117 may mate with, ore register with, or align with the one or more air inlets 28, 38 on the inhaler body.

The nicotine powder delivery consumable or receptacle article 100 may be a modular or a replaceable component of a multi-use inhaler 10.

The invention claimed is:

1. An inhaler system suitable for providing nicotine particles, comprising:
an inhaler body extending from a mouthpiece end to a distal end, the inhaler body comprising a mouthpiece portion removably coupled to a distal end portion, the mouthpiece portion extending between the mouthpiece end and a first mating end, the distal end portion extending between a second mating end and the distal end,
the mouthpiece portion comprising:
a capsule cavity defined within the first mating end;
a mouthpiece air channel extending from the mouthpiece end to the capsule cavity;
the distal end portion comprising:
a resealable membrane sealing the capsule cavity at the first mating end; and
a piercing element coupled to the distal end portion, the piercing element being configured to move between a relaxed position and a piercing position, the piercing element extending through the resealable membrane and into the capsule cavity in the piercing position; and
a receptacle disposed within the capsule cavity, the receptacle being a replaceable article of the inhaler system, the receptacle comprising a pierceable membrane sealing a receptacle first end;
wherein the resealable membrane is configured to reseal when the piercing element moves from the piercing position to the relaxed position where the piercing element is spaced apart from the resealable membrane,
wherein the resealable membrane contacts the piercable membrane of the receptacle, and
wherein a capsule is disposed within the receptacle, the capsule being configured to rotate about a longitudinal axis of the capsule while disposed in the receptacle.

2. The inhaler system according to claim 1, wherein the receptacle defines an air outlet at a receptacle second end opposite of the receptacle first end, and the receptacle includes an air inlet.

3. The inhaler system according to claim 2, wherein the capsule contains solid particles comprising nicotine.

4. The inhaler system according to claim 2, wherein the inhaler body comprises an air inlet that is in fluid connection with the air inlet of the receptacle.

5. The inhaler system according to claim 2, wherein the air outlet of the receptacle is in fluid connection with the mouthpiece air channel.

6. The inhaler system according to claim 1, wherein the resealable membrane is fixed to the second mating end of the distal end portion.

7. The inhaler system according to claim 1, wherein the resealable membrane is a septum element.

8. The inhaler system of claim 1, wherein the inhaler body comprises a side wall forming the capsule cavity and an inhaler air inlet extending through the side wall, wherein the receptacle comprises a receptacle air inlet, and wherein the inhaler air inlet is aligned with the receptacle air inlet.

9. The inhaler system of claim 8, wherein the inhaler air inlet is constructed to register with the receptacle air inlet.

10. The inhaler system of claim 8, wherein the inhaler air inlet is closer to the receptacle first end than a second receptacle end.

11. The inhaler system of claim 10, wherein the inhaler air inlet is disposed within 5 mm of the receptacle first end.

12. The inhaler system of claim 1, wherein the receptacle comprises a receptacle air outlet that aligns with the mouthpiece air channel.

* * * * *